United States Patent [19]

Partyka et al.

[11] 4,105,695
[45] Aug. 8, 1978

[54] 2-AMINO-1-(2,5-DIMETHOXYPHENYL)-BUTANES

[75] Inventors: Richard Anthony Partyka, Liverpool; Robert Ted Standridge, Cazenovia; Henry George Howell, East Syracuse, all of N.Y.; Alexander Theodore Shulgin, Lafayette, Calif.

[73] Assignee: Bristol-Myers Company, New York, N.Y.

[21] Appl. No.: 795,699

[22] Filed: May 11, 1977

Related U.S. Application Data

[63] Continuation-in-part of Ser. No. 639,676, Dec. 11, 1975, abandoned.

[51] Int. Cl.$^2$ .............................................. C07C 87/28
[52] U.S. Cl. .................... 260/570.8 R; 260/326 R; 260/326 S; 260/326 A; 260/599; 260/609 R; 260/612 D; 424/316; 424/330
[58] Field of Search ..................... 260/570.8 R, 501.17

[56] References Cited
U.S. PATENT DOCUMENTS 3,655,737   4/1972   Carlsson et al. ................. 260/501.17

OTHER PUBLICATIONS

Barfknecht et al. "Jour. of Med. Chem.", vol. 14, No. 4, pp. 370–372 (1971).

Shulgin, "Chemical Abstracts", vol. 81, p. 481, Section 104988s (1974).

*Primary Examiner*—Robert V. Hines
*Attorney, Agent, or Firm*—Richard R. Lloyd

[57] ABSTRACT

Compounds of the formula

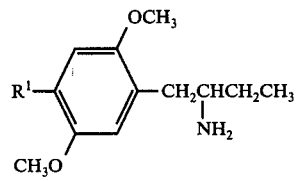

wherein $R^1$ is Cl, Br, (lower)alkylthio or

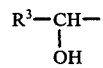

in which $R^3$ is H or (lower)alkyl including the racemic mixtures and the dextrorotatory and levorotatory isomers, and the pharmaceutically acceptable non-toxic salts thereof have been found to enhance the learning capacity of mammals, including man, and to improve the mental alertness and attitudes of geriatrics without producing the undesirable stimulant side effects associated with the use of amphetamines.

4 Claims, No Drawings

2-AMINO-1-(2,5-DIMETHOXYPHENYL)-BUTANES

CROSS-REFERENCE TO RELATED APPLICATION

This application is a continuation-in-part of our copending application Ser. No. 639,676 filed Dec. 11, 1975 and now abandoned.

BACKGROUND OF THE INVENTION

1. Field of the Invention

This invention relates to novel compounds which are useful for enhancing the learning capacity of mammals, including man, and they have been found to have a profound beneficial effect in human geriatric patients by increasing their mental alertness and improving their mental attitude and physical appearance without the undesirable stimulant side effects commonly associated with amphetamines.

In another aspect, this invention relates to a method of preparing the novel compounds. In still another aspect, this invention relates to a method of enhancing the learning capacity of mammals. In a further aspect, this invention relates to compositions useful in the method of enhancing the learning capacity of mammals.

2. Description of the Prior Art

Numerous compounds structurally related to amphetamine (α-methylphenethylamine) have been prepared and reported in the literature and are the subject matter of various patents. Of particular interest with respect to the compounds disclosed herein are U.S. Pat. No. 3,547,999, Shulgin, A. T.: Chemistry and Structure-Activity Relationships of the Psychotomimetics which appeared in the book, Psychotomimetic Drugs, Ed. D. H. Efron, Raven Press 1970 and Shulgin, A. T., Sargent, T. and Naranjo, C.: Structure-Activity Relationships of One-Ring Psychotomimetics, Nature, 521-537 (1969). The foregoing patent and references disclose compounds closely related to the compounds of this invention. However, none of the compounds is disclosed as having the activity of the compounds of this invention. The Shulgin article in Psychotomimetic Drugs at pages 35-36 indicates that a "four chain compound" had been synthesized; however, the particular compound synthesized is not named, the structure is not disclosed, the method of preparation is not disclosed and no utility is disclosed in the article.

(3) Other patents and publications reported from a search are U.S. Pat. No. 2,246,529; Journal of the American Chemical Society, Vol. 78, pages 4419-22 (1956); Journal of Medicinal Chemistry, Vol. 9, No. 4, pages 469-70 (1966); Arch. int. Pharmacodyn Vol. 154; No. 1, pages 26, 31-32 (1965); Chemical Abstracts, Vol. 61, page 6954a; Chemical Abstracts, Vol. 71, page 12786q; Chemical Abstracts, Vol. 67, pages 10215w; Chemical Abstracts, Vol. 72, page 12364w; and Chemical Abstracts, Vol. 59, page 3797d.

Belgian Pat. No. 806,990 describes and claims the compounds having the formula

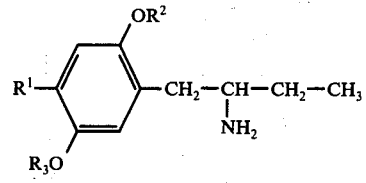

wherein $R^1$, $R^2$ and $R^3$ are alike or different and each is (lower)alkyl. The patent describes a method of preparation that is non-stereospecific.

D. E. Nichols, C. F. Barfkneckt and D. B. Rusterholz describe the "Asymmetric Synthesis of Psychotomimetic Phenylisopropylamines" in the Journal of Medicinal Chemistry, 1973, Vol. 16, No. 5, 480-483.

C. F. Barfknecht and D. E. Nichols, in J. Medicinal Chemistry, 14, 370-2 (1971), disclose inter alia the compound of the formula

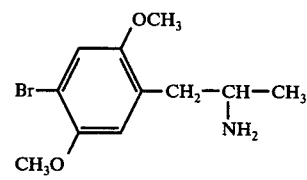

which is the lower homolog of one of the compounds claimed herein. However, unlike the compounds of the present invention, that compound was disclosed as having mescaline-like side-effects which are much more profound than those produced by DOM.

Chemical Abstracts, 81, 104988s (1974) (corresponding to West German OLS No. 2,355,350) discloses the compound of the formula

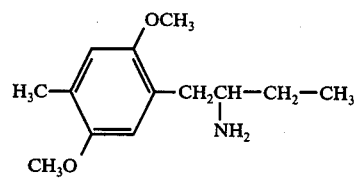

as the racemate and the optically active antipodes. The compound improved the chronic avoidance aquisition of rats.

U.S. Pat. No. 3,457,354 discloses compounds of the formula

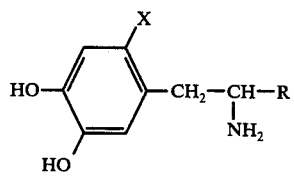

in which X is —OH or —$NH_2$ and R is H, —$CH_3$ or —$C_2H_5$ as antihypertensive agents.

U.S. Pat. No. 3,655,737 discloses compounds of the formula

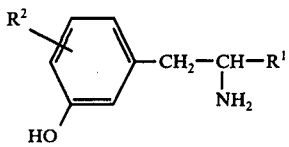

in which R$^1$ is —CH$_3$, —C$_2$H$_5$ or —C$_3$H$_7$ and R$^2$ (in position 2, 4, 5 or 6) is F, Cl, Br, —CH$_3$, —C$_2$H$_5$ or —C$_3$H$_7$ as antihypertensive and antidepressant agents.

A. T. Shulgin, in Experientia, 19, 127–8 (1963), reports the testing of a series of mescaline homologs of the formula

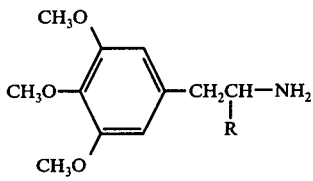

in which R varied from H through C$_7$H$_{15}$. He reports that toxicity and behavioral studies with mice could not distinguish between the first three members of this series (i.e. the ethylamino, propylamino and butylamino compounds). In humans it is established that the compound in which R is CH$_3$ (the propylamino compound) is more than twice as potent as mescaline (R = H; the ethylamino compound), but Shulgin found that the compound in which R = C$_2$H$_5$ (the butylamino compound) produced neither central nervous system activity nor psychtotomimetic (hallucinogenic) disturbance. Surprisingly, the compounds of the present invention have been found to possess the desirable central nervous system activity (e.g. enhancement of learning capacity and improvement of mental alertness) without the undesirable psychotomimetic side-effects.

SUMMARY OF THE INVENTION

The compounds having the formula

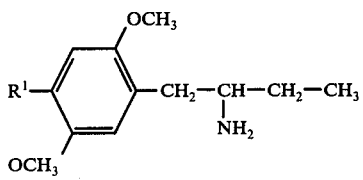

wherein R$^1$ is Cl, Br, (lower)alkylthio or

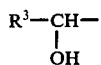

in which R$^3$ is H or (lower)alkyl; or a pharmaceutically acceptable non-toxic salt thereof have been found to enhance the learning capacity of mammals, including man, and to improve the mental alertness and attitudes of geriatrics without producing the undesirable stimulant side effects associated with the use of amphetamines.

COMPLETE DISCLOSURE

There is provided according to the present invention a pharmaceutical composition useful for enhancing the learning capacity of mammals which comprises an effective amount of a compound of the formula

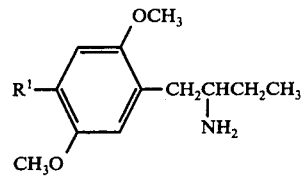

wherein R$^1$ is Cl, Br, (lower)alkylthio or

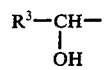

in which R$^3$ is H or (lower)alkyl; or a pharmaceutically acceptable nontoxic salt thereof and a pharmaceutically acceptable carrier.

Another aspect of this invention is the provision of a method of enhancing the learning capacity of mammals, including man, which comprises administering to said mammal an effective amount, of a compound of formula I or a pharmaceutically acceptable nontoxic salt thereof.

A further aspect of this invention is the provision of a method of treating despondent, psychotic, schizophrenic, manic depressive and senile geriatric humans, which comprises administering to said humans an effective amount of a compound of formula I, or a pharmaceutically acceptable nontoxic salt thereof. The treatment of patients suffering the above-described symptoms results in the patients exhibiting near-normal behavior patterns.

The compounds of formula I contain an asymmetric carbon atom and thus normally occur as a racemic mixture of the dextro- and levorotatory optical isomers. Both and dextro- and levorotatory isomers of these compounds, as well as the racemic mixtures are useful in the composition and method described above and are considered to be an integral part of the invention.

A further aspect of this invention is the provision of the dextro- and levorotatory isomers of the compounds of formula I; and the pharmaceutically acceptable nontoxic salts thereof.

The pharmaceutically acceptable nontoxic salts include the organic and inorganic acid addition salts, e.g., those prepared from acids such as hydrochloric, sulfuric, sulfonic, tartaric, fumaric, hydrobromic, hydriodic, glycolic, citric, maleic, phosphoric, succinic, acetic and the like. Such salts are prepared by conventional methods by reacting the free base with the desired acid on about an equivalent basis.

The term "(lower)alkyl" as used herein includes both straight chain and branched chain alkyl radicals containing from 1 to 4 carbon atoms, e.g., methyl, ethyl, propyl, isopropyl, butyl, sec-butyl, isobutyl and t-butyl.

A preferred embodiment of the instant invention is the compound having the formula

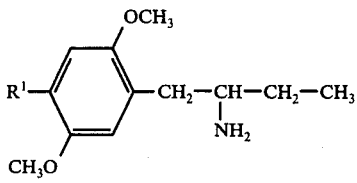

wherein $R^1$ is Cl, Br, —SCH₃ or —CH₂OH; or a pharmaceutically acceptable nontoxic salt thereof.

A more preferred embodiment is the compound of formula I wherein $R^1$ is Cl.

Another more preferred embodiment is the compound of formula I wherein $R^1$ is Br.

Another more preferred embodiment is the compound of formula I wherein $R^1$ is —SCH₃.

Another more preferred embodiment is the compound of formula I wherein $R^1$ is —CH₂OH.

A more preferred embodiment is the essentially pure dextrorotatory or levorotatory isomer of the compound having formula I supra.

The most preferred embodiment is the levorotatory isomer of compound I supra.

When the process illustrated in Scheme II is employed, the compounds I are stereoselectively prepared as either the R or S isomer. When the synthesis employed is non-stereospecific, the compounds I are obtained as racemic mixture which must then be resolved if one desires to obtain the essentially pure R and S optical isomers.

The racemic compounds of formula I may be resolved by forming a mixture of the two diastereoisomeric salts of said compounds with a dextrorotatory or levorotatory ring-substituted tartranilic acid, e.g., nitro, chloro or bromo substituted, separating said diastereoisomeric salts by fractional crystallization and converting the separated diastereoisomeric salts to the respective optical isomers of the compound preferably by treatment with a strong base, e.g., sodium carbonate, potassium carbonate and the like. (+)-2'-Nitrotartranilic acid and (+)-2'-chlorotartranilic acid are particularly useful in the resolution of the racemic compounds of Formula I. The general resolution procedure using tartranilic acids is described in U.S. Pat. No. 3,452,086 by T. A. Montzka et al, J. Org. Chem. 33, 3993 (1968).

The compounds of formula I in the form of racemic mixtures or their dextrorotatory or levorotatory isomers possess learning enhancement activity making them useful for enhancing the learning capacity of mammals. The compounds while structurally related to amphetamine do not produce amphetamine-like central nervous system stimulant activity in mammals.

The compounds of the invention were tested in a primary mouse screen[1] as illustrated in Table I. Most of the compounds exhibited some degree of stimulation which were characterized by clonic convulsions, tremors, irritability and ataxia when given orally at the indicated doses (mg/kg).

[1] S. Irwin, Psychopharmacol. 13, 222 (1968).

These agents were also compared to R-2,5-dimethoxy-4-methylamphetamine (R-DOM) in terms of affecting cat behavior[2]. DOM-like activity was described as depression, dissassociation from the enviroment, catatonia, diarrhea, miosis, salivation, piloerection, arched back, and muscle rigidity. Reference compound (—)-2-amino-1-(2,5-dimethoxy-4-methylphenyl)butane hydrochloride (BL-3912A) had no effect on the behavior of the cat at 5–10 mg. mg./kg. s.c., while resulting in alertness, piloerection, mydriasis and some arching at 20 mg./kg. The results are found in Table I.

[2] M. B. Wallack et al, J. Pharm. Exp. Thera. 182, 145 (1972).

TABLE 1

| Compound No. | Mouse CNS Screen, mg/kg po | Cat Behavior, mg/kg sc |
|---|---|---|
| 1 | 300 - toxic, 50, 150 - stimulation | 10 - no DOM-like effects |
| 2 | 300, 150 - stimulation | 10 - no DOM-like effects |
| 3 | 300 - toxic, 100 - stimulation | 10 - no DOM like effects |
| 4 | 300 - toxic; 150 - stimulation | 10 - weak DOM-like effects |
| 5 | 300, 150 - weak stimulation | 10 - questionable Dom-like effects |
| 6 | 300 - toxic, convulsant; 150, 50 - stimulation | 10 - questionable or weak DOM-like effects |
| 7 | 300 - tremors, stimulation; 150, 50 - stimulation | 10 - questionable DOM-like effects |
| 8 | 300 - no effects | 10 - no DOM-like effects |
| 9 | 300 - no effects | 10 - no DOM like effects |
| 10 | 300 - no effects | 10 - no DOM-like effects |
| 12 | 300 - initial (10–30 min) ataxia, jumping motions tremors and shaking; no significant effects for next 3 hours 150 - no significant effects | 10 - no DOM-like effects |

Remarks:
A. In general, most the compounds exhibited predominantly stimulant effects in the mouse CNS screen.
B. Some of the compounds exhibited signs of DOM-like effects in the cat. However, they were weak and incomplete as compared to those seen with DOM.

One of the preferred compounds of the present invention (the 4-methylthio compound; BL-5485A) was compared with R-DOM for the facilitation of avoidance acquisition. The test animals were retired breeder rats of the Long-Evans strain (Blue Spruce Farms, Altamont, N.Y.). Experiments were conducted in automated shuttle cages (BRS/LVE, Model No. 146-04) contained within a light and sound-attenuated chamber equipped with a ventilation fan. Control of the shuttle box and recording of responses were accomplished by means of standard electromechanical modules. Injection of drugs i.p. and placement of the subjects into the shuttle cage were followed by a 1-minute pre-session acclimation period. The first avoidance trail was then initiated by activating a white light on the side of the shuttle cage occupied by the subject. If the animal did not cross to the other side of the chamber within 5 seconds (avoid), the grid floor under the animal was electrified with 0.8 mA of scrambled shock (BRS/LVE, Model No. 1531 shocker). Each subject received 120 avoidance trials during a 1 hour session. The results of the test are shown in Table II.

TABLE II

| Compound | Dose, i.p. (mg./kg.) | N | Avoidance Response (Mean ± S.E.) |
|---|---|---|---|
| Saline | — | 15 | 57.7 ± 4.1 |
| BL-5485A | 5 | 8 | 70.5 ± 10.4 |
| BL-5485A | 10 | 7 | 89.0 ± 3.3 |
| BL-5485A | 20 | 8 | 77.5 ± 6.7 |
| Vehicle | — | 24 | 46.0 ± 6.5 |
| R-DOM | 0.5 | 8 | 70.9 ± 4.8 |
| R-DOM | 1 | 8 | 36.1 ± 4.5 |
| R-DOM | 5 | 8 | 13.8 ± 7.3 |

Table II shows that BL-5485A increased avoidance response at all doses tested while R-DOM increased avoidance response at one dosage and reduced it at all other doses tested.

More specific tests also were employed to determine the presence or absence of undesirable psychotomimetic activity in the compounds of this invention. The test procedure is a modification of that described by Wallach et al. in J. Pharmacol. Exp. Ther. 182, 145-154 (1972).

Various compounds are known to produce sensory distortions in man and characteristic responses in the cat. These psychotomimetic effects (so-called hallucinogenic effects) in a compound under test are often compared with the effects produced by R-2-amino-1-(2,5-dimethoxy-4-methylphenyl)propane (usually referred to as R-DOM). R-DOM is Compound 1 in the Table below, and was used as a comparison standard in the test.

Adult female cats are housed in a large communal cage. On test day the animals are transferred to the observation room and placed into separate cages approximately 12–15 sq. feet in floor area with front wired door allowing observation of the cats. The animals can ally corresponds to the time of peak effects induced by a compound. The effects are scored utilizing a check list containing 12 categories, each of which contains 2 sub-categories. Each sub-category is worth 1 point, giving a maximum numerical score of 24. The categories and sub-categories are as follows:

1. Body Posture: Arched Back/Stiff Tail
2. Extension of Limbs: Legs/Legs and Toes
3. Muscle Rigidity: Legs/Abdomen
4. Abnormal Leg Position/Immobility
5. Motor Coordination: Ataxia/Loss of Righting Reflex
6. Open Mouth/Protruding Tongue
7. Claws Out/Attempts To Bite or Claw
8. Teeth Baring/Hissing or Growling
9. Contact with Environment: Reduced/Absent
10. Piloerection: Tail/Back
11. Pupillary Constriction: Moderate/Extreme
12. Salivation/Emesis In addition to the above-described tests in cats, a hyperthermia test in rabbits was run with certain of the compounds. The ability of hallucinogenic phenylalkylamines to increase the rectal temperature of rabbits at low doses is well established (Aldous et al., 1974). The hyperthermia test is not absolutely predictive of the presence of psychotomimetic activity in a given compound, because this test detects some compounds which prove to be lacking psychotomimetic activity upon further evaluation. Nevertheless, this method provides a reliable quantitative measure of relative psychotomimetic potencies of compounds in a given series or once a given compound has been shown by other tests (as is here the case) to have such activity.

The results of the foregoing test procedures are summarized in the following Table III. It should be noted that the test compounds were administered at 10 mg/kg while the comparison compounds, because of their high psychotomimetic activity were administered at 1 mg/kg.

TABLE III

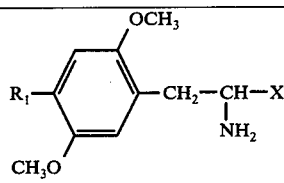

| Test Compound | $R^1$ | X | Isomer | Dose In Cats (mg./g.; s.c.) | Effect In Cats (Score)[a] | Hyperthermia In Rabbits (i.v. dose for 1° C rise; mg./kg.) |
|---|---|---|---|---|---|---|
| A (R-DOM) | $CH_3$ | $CH_3$ | R | 1 | 13.3 ± 1.8 (N = 4) | 0.04 (0.04)[c] |
| B (BL-3912A) | $CH_3$ | $C_2H_5$ | R | 10 | 1.3 ± 0.5 (N = 4) | 1.00 |
| C | Cl | $CH_3$ | R, S | 1 | 11.5 (N = 2; 10, 13)[b] | 0.01[c] |
| D | Cl | $C_2H_5$ | R | 10 | 6.5 (N = 2; 6, 7) | not done |
| E | Br | $CH_3$ | R | 1 | 17.5 (N = 2; 17, 18) | 0.01[c] |
| F | Br | $C_2H_5$ | R | 10 | 3.5 ± 0.9 (N = 4) | 0.80 |
| G | $CH_3S$ | $CH_3$ | R, S | 1 | 11 (N = 2; 9, 13) | not done |
| H | $CH_3S$ | $C_2H_5$ | R | 10 | 0 (N = 2; 0, 0) | not done |
| I | $CH_2OH$ | $C_2H_5$ | R | 10 | 0.5 (N = 2; 0, 1) | not done |

[a]Total score in test described in text (mean ± S.E.M.).
[b]Any mean with less than three subjects have the individual values in parentheses.
[c]Aldous, et al., J. Med. Chem., 17, 1100 – 1111 (1974).

see the experimenter and each other across the room, and may have auditory and olfactory contact among themselves in adjacent cages. The experimental subjects are accustomed to this environment and settle down rapidly (< 30 min.) after being brought in.

The test compounds (initially 10 mg./kg.) are administered subcutaneously into the back of the neck. Following the dosing animals (N=2-4) are observed for 3 hrs. but the scoring is usually done at 1 hr. which usu- The results obtained in these tests show that:
1. R-DOM produced marked psychotomimetic effects in the cat at 1 mg./kg..
2. Test Compounds C, E and G, having α-methyl substitution on the aliphatic side-chain like R-DOM, have psychotomimetic effects in the cat which are very similar (in terms of potency and quality) to that of R-DOM.
3. Test Compounds B, D, F, H and I, having α-ethyl substitution on the aliphatic side-chain, exhibit practically no psychotomimetic effects (in the case of Compounds B, F, H and I) or a psychotomimetic effect which is approximately 18 times weaker than R-DOM (in the case of Compound D).
4. The hyperthermia tests indicate that the psychotomimetic activity of Compound F (α-ethyl substitution on the aliphatic side-chain) is 80 times weaker than its lower homolog (Compound E) and 20 times weaker than R-DOM.

Thus, highly significant decreases in psychotomimetic properties (or the virtual absence thereof) were demonstrated in the 4-chloro-, 4-bromo-, 4-methylthio- and 4-hydroxymethyl-compounds containing α-ethyl substitution on the aliphatic side-chain, when compared with their correspondingly 4-substituted lower homologs containing α-methyl substitution on the aliphatic side-chain and/or with R-DOM.

The large decrease in psychotomimetic activity of the compounds of this invention as compared with their corresponding lower homologs is particularly surprising in view of Shulgin et al., Nature, 221, 537-541 (1969), cited above. Those authors compared the psychotomimetic activity of a large number of substituted phenylalkylamines and found significant changes in psychotomimetic activity with changes of substituents and position of substitution on the phenyl ring, and also when increasing the side chain from ethylamino to propylamino. Only two of their compounds contained the same substitution in the phenyl ring, but with propylamino and butylamino side chains, respectively, namely compounds of the formula

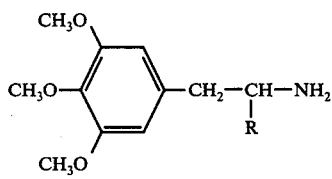

in which R was $CH_3$ (their compound VIII) and $C_2H_5$ (their compound XLIII). The activities of these compounds (reported as Mescaline Units; number of times as active as mescaline) were 2.2 M.U. for the propylamino compound and <2 M.U. for the butylamino compound. The authors stated that "there seems to be a decrease" in psychotomimetic activity in going from propylamino to butylamino, but cautioned that the M.U. values should not be considered accurate to closer than ± 25%.

The compound BL-3912A, a reference compound used in assaying the compounds of this invention, has demonstrated remarkable and profound effects in initial clinical studies in psychotics and normal senile geriatric patients. For example, in psychotics demonstrating schizophrenia and manic depression, a dose of 50 to 100 mg per day produced remarkable results in that virtually all the patients so treated behaved in a near normal manner. The catatonics relaxed, the withdrawn and fearful became sociable, etc.

In the non-psychotic geriatric patient, at a dose of 25 to 50 mg/day, BL-3912A had the effect of producing increased mental alertness and a renewed interest in life characterized by increased sociability, mobility, concern about appearance, dress and general well-being.

In two instances where the patient had Parkinson's disease, substantially complete remission of the symptoms of the disease was observed at a dose of 100 mg/day.

The ability of BL-3912A to increase the learning capacity of humans has been confirmed in the initial clinical trials.

In view of all the above and in projecting the activity found in rodents to humans, it is anticipated the compounds of the instant invention will possess activity in man that is essentially identical to that seen for BL-3912A.

The compounds I of the instant invention can be prepared by several alternative methods as illustrated by the following diagramatic schemes:

Scheme I:

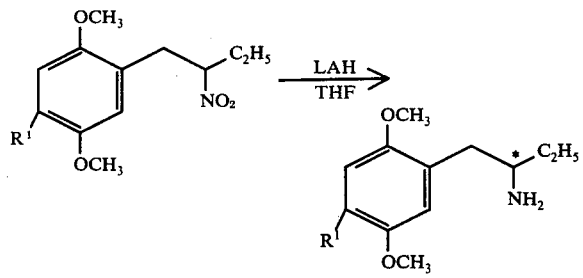

wherein $R^1$ is as defined above; followed by resolution into the D and L isomers.

Scheme II:

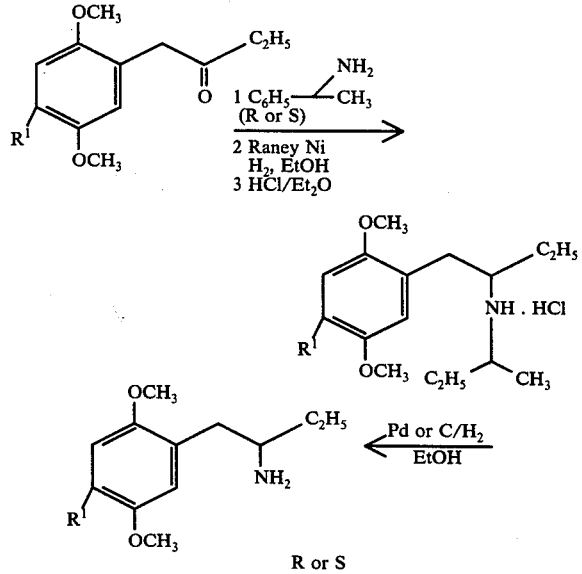

R or S

The isomer obtained has the same absolute configuration as the α-methylbenzylamine employed.

Scheme III:
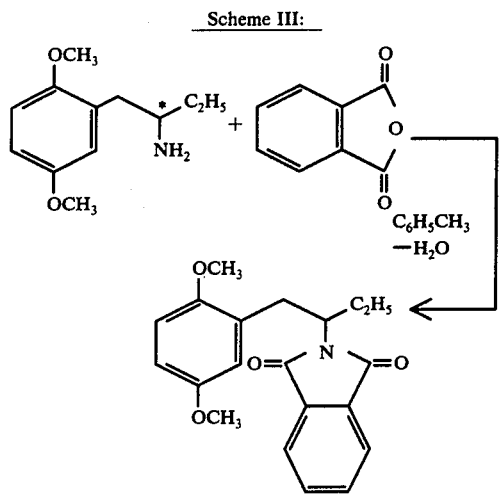
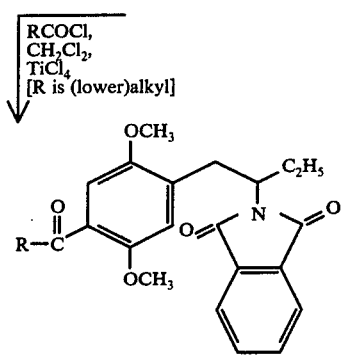
Scheme IV:
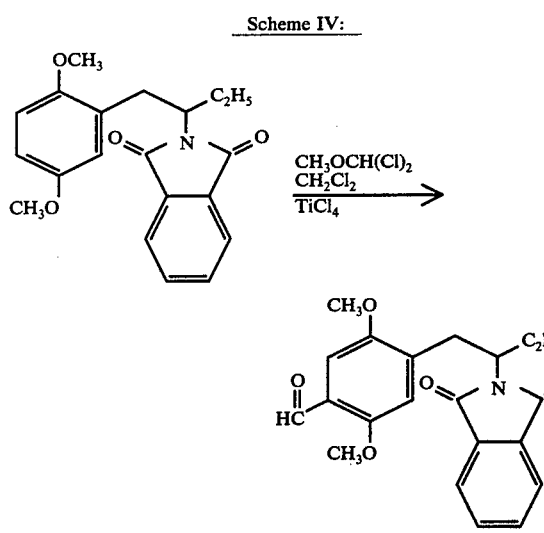
Scheme V:
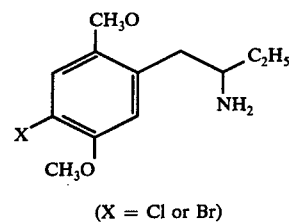
(X = Cl or Br)
Scheme VI:
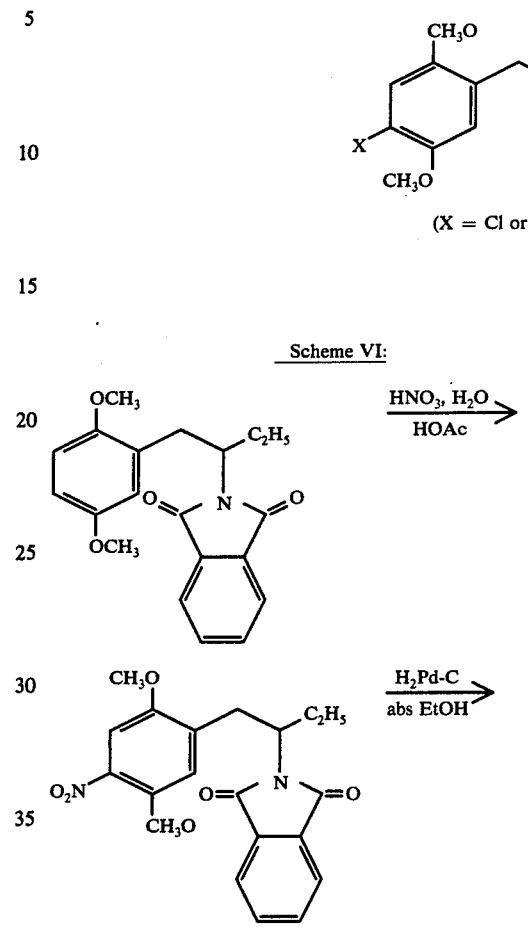
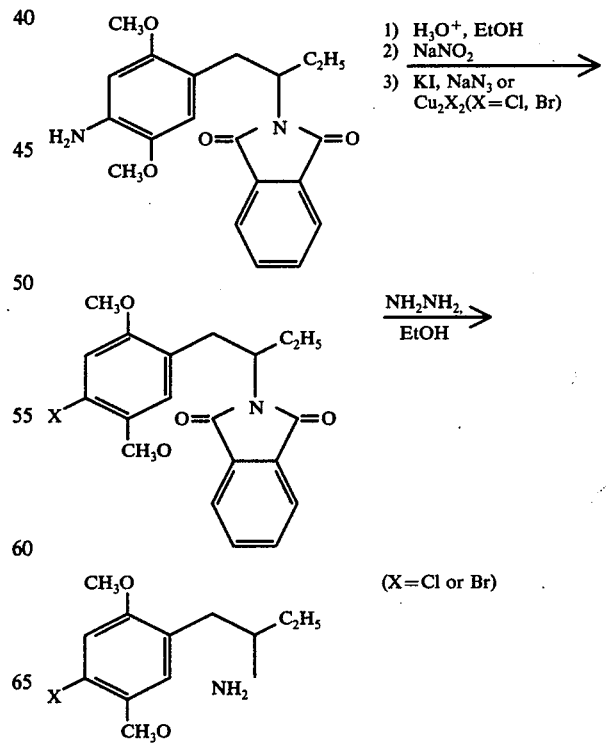
(X = Cl or Br)

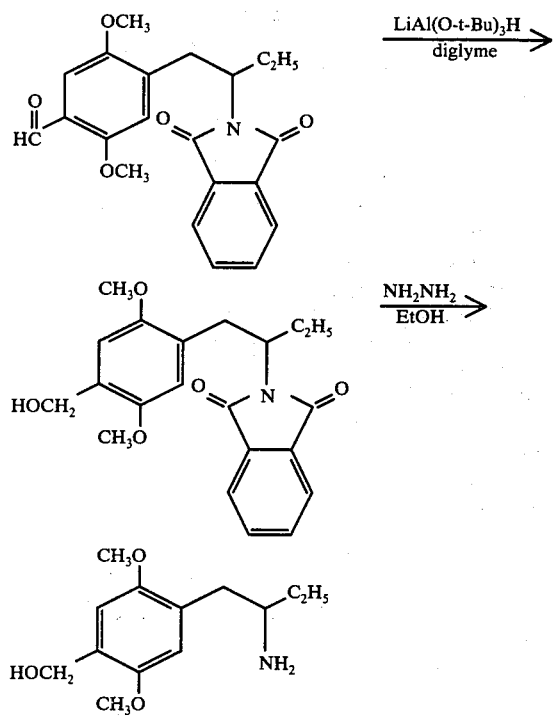

Scheme VIII:

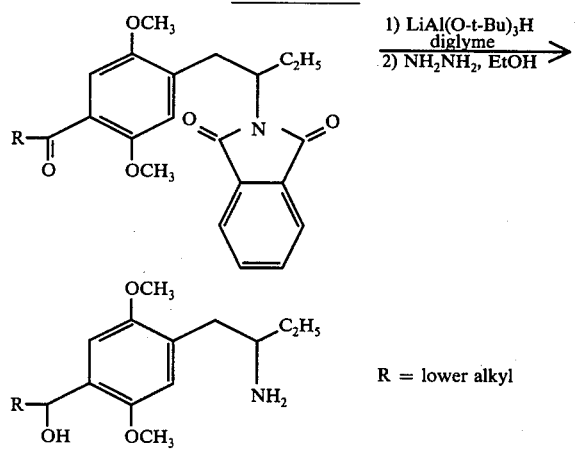

R = lower alkyl

Scheme IX:

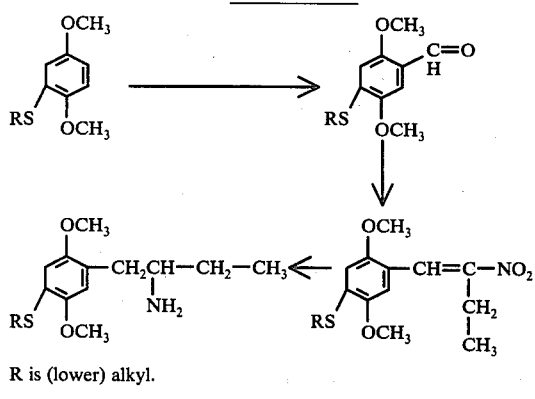

R is (lower) alkyl.

EXAMPLE 1

(±)-2-Amino-1-(2,5-dimethoxyphenyl)butane hydrochloride (1).

A suspension of 22.8 g (0.60 mole) of powdered LaH (lithium aluminum hydride) in 400 ml of anhydrous THF (tetrahydrofuran) was stirred and refluxed for 30 mins. A solution of 23.73 g (0.10 mole) of 1-(2,5-dimethoxyphenyl)-2-nitro-1-butane in 100 ml of anhydrous THF was then added dropwise at reflux. After addition was complete, the mixture was stirred and refluxed for 24 hrs. The reaction mixture was cooled to 0° and then was decomposed by the cautious dropwise addition, with rapid stirring, of 25 ml of $H_2O$ and 100 ml of THF. The cooling bath was removed and 25 ml of 10% NaOH solution, followed by 25 ml. of $H_2O$ was added dropwise; the mixture was stirred until a granular white solid was obtained. The inorganic salts were filtered and washed well with THF.

The filtrate was evaporated and the oil thus obtained was partitioned between very dilute NaOH solution and $Et_2O$. The layers were separated and the aqueous was extracted well with $Et_2O$. The combined organic extracts were washed with $H_2O$ and with saturated brine and dried over anhydrous $Na_2SO_4$. The desiccant was filtered, the filtrate was evaporated to ca. 100 ml., and the salt was precipitated with HCl (g). The solvent and excess HCl were removed under reduced pressure and the residue was flashed down twice with EtOAc. The solid was recrystallized from $CH_3CN$ to give 9.71 of title product as colorless crystals; mp 175°–177°. The filtrate was cooled and saturated with HCl (g) to give an additional 4.0 g of product. The total yield was 13.71 g (56%).

Anal. Calc'd. for $C_{12}H_{19}NO_2.HCl$: C, 58.65; H, 8.20; N, 5.70; Cl, 14.42. Found: C, 58.65; H, 8.14; N, 5.91; Cl, 13.96.

EXAMPLE 2

1-(2,5-Dimethoxy-4-formylphenyl)-2-(N-phthalimido)-butane.

a. R-isomer

A stirred solution, under $N_2$, of 9.2 g (27 mmoles) of R-1-(2,5-dimethoxyphenyl)-2-(N-phthalimido)butane in 75 ml of anhydrous $CH_2Cl_2$ was maintained at 0° while 5 ml (8.63 g., 45 mmoles) of $TiCl_4$ was added dropwise. α,α-Dichloromethylmethyl ether (3.1 g., 27 mmoles) was then added, dropwise, at 0°. The reddish-brown solution was stirred at 0° for 30 mins.; the temperature was raised to 25° over a period of 15 mins. The solution was then stirred at 35° for 15 mins. and then refluxed for 15 mins. The reaction mixture was then poured into 200 ml of ice $H_2O$. The layers were separated and the aqueous was extracted with 3 portions of $CH_2Cl_2$. The combined organic solutions were washed with $H_2O$ and saturated brine and dried over anhydrous $Na_2SO_4$. Removal of the solvent gave 9.6 g of greenish oil. Upon seeding, the oil crystallized. Recrystallization from MeOH $H_2O$ gave 6.36 g. of title product as colorless crystals; mp 111°–113°, $[\alpha]_D^{24.8}$ −258.6° (c=1.0, 95% EtOH).

The product was initially obtained crystalline by chromatography of 2.0 g of the crude oil on 150 g of neutral silica gel packed into a 4 cm column. The column was eluted with Skellysolve B containing increasing proportions of $CH_2Cl_2$ and finally with pure $CH_2Cl_2$. Evaporation of the combined fractions containing the compound first eluted gave 1.35 g. (67%) of an oil which crystallized upon standing.

b. Racemic Mixture

Substitution in the procedure of step a for the R-1-(2,5-dimethoxyphenyl)-2-(N-phthalamido)butane used therein of an equimolar quantity of the racemic 1-(2,5-dimethoxyphenyl)-2-(N-phthalimido)butane produced the racemic title compound.

The crude oily product was chromatographed on 1 kg of Woelm Activity III neutral alumina packed into a 9 cm column. The column was eluted with Skellysolve B containing progressively greater proportions of $CH_2Cl_2$ (5, 10, 15, 25 and finally 50%). The product began to appear in fractions containing 25% $CH_2Cl_2$. The fractions were combined and solvents evaporated to give 21.61 g of an oil. This was dissolved in 150 ml of hot 95% EtOH and the solution was incubated at room temperature for 24 hrs. and then at $-15°$ for 48 hrs. Large, slightly greenish crystals were obtained; 15.97 g (43%), mp 92°–96°.

Anal. Calc'd. for $C_{21}H_{21}NO_5$: C, 68.65; H, 5.76; N, 3.81. Found, R-isomer: C, 68,84; H, 5.77; N, 3.79. Found, racemic: C, 68.35; H, 5.80; N, 3.73.

EXAMPLE 3

1-(2,5-Dimethoxy-4-hydroxymethylphenyl)-2-(N-phthalimido)butane.

a. R-isomer

To a stirred solution of 3.75 g (10.2 mmoles) of R-1-(2,5-dimethoxy-4-formylphenyl)-2-(N-phthalimido) butane in 100 ml of anhydrous diglyme was added 3.57 g (17.3 mmoles) of lithium tri-t-butoxyalumino hydride. The solution was stirred at room temperature for 64 hrs. The mixture was poured onto ice and 5% HCl and the product was extracted out with $Et_2O$. The organic solution was dried (anhydrous $Na_2SO_4$) and evaporated. The residue was stripped under high vacuum to give 4.75 g of a light green oil.

The product was crystallized from EtOAc-Skellysolve B to give 2.13 g (57% yield) of title product; mp 111-113°; $[\alpha]_D^{24}$ −178.0° (c=0.5, 95% EtOH).

b. Racemic Mixture

Substitution in the procedure of step a for the R-1-(2,5-dimethoxy-4-formylphenyl)-2-(N-phthalimido) butane used therein of an equimolar quantity of the racemic 1-(2,5-dimethoxy-4-formylphenyl)-2-(N-phthalimido)butane produced the racemic title compound as colorless crystals from EtOAc-Skelly B; mp 89°–91°.

Anal. Calc'd. for $C_{21}H_{23}NO_5$: C, 68.28; H, 6.28; N, 3.79. Found, R-isomer: C, 67,98; H, 6.32; N, 3.80. Found, racemic: C, 67.86; H, 6.28; N, 3.78.

EXAMPLE 4

R-2-Amino-1-(2,5-dimethoxy-4-hydroxymethylphenyl)-butane (17).

A solution of 2.09 g (5.67 mmoles of R-1-(2,5-dimethoxy-4-hydroxymethylphenyl)-2-(N-phthalimido)-butane and 2.1 ml (2.12 g., 66.2 mmoles) of 95% hydrazine in 75 ml of absolute EtOH was refluxed for 2.5 hrs. The mixture was evaporated to dryness and the residue was flashed down with 2 portions of toluene. The solid was triturated with dil HCl and filtered. The filtrate was made basic with NaOH solution and extracted with $Et_2O$. The combined extracts were washed with $H_2O$ and with saturated brine and dried (anhydrous $Na_2SO_4$). Evaporation of the solvent gave 1.12 g (82%) of a colorless solid, the title compound, which was pure by glc.

An analytical sample was recrystallized from EtOAc-Skellysolve B; mp 85°-86°.

Anal. Calc'd. for $C_{13}H_{21}NO_3$: C, 65.24; H, 8.85; N, 5.85. Found: C, 65.21; H, 8.68; N, 5.55.

EXAMPLE 5

R-2-Amino-1-(4-bromo-2,5-dimethoxyphenyl)butane hydrochloride (11).

To a stirred solution of R-2-amino-1-(2,5-dimethoxyphenyl)butane (obtained from 20.0 g (81.6 mmoles) of the corresponding hydrochloride in 150 ml of glacial HOAc was added dropwise at $-10°$ C., a solution of 13.1 g. (82 mmole) of $Br_2$ in 50 ml. of glacial acetic acid. After addition was complete, the solution was stirred at $-10°$ for 1 hr.; the reaction mixture solidified. The cooling bath was removed and the reaction mixture stood at room temperature for 40 hrs.

The mixture was diluted with 150 ml. of $Et_2O$ and allowed to stand for 2 hrs. The white solid was filtered, washed with $Et_2O$, and dried to give 22.65 g. of the hydrobromide salt of the product. The hydrobromide was converted to the free base and the salt was formed with HCl (g) in anhydrous $Et_2O$. The crude material was recrystallized from IPA to give 18.8 g (71%) of the title compound as colorless crystals; mp 240°–242°; $[\alpha]_{365}^{24}$ −58.0° (c=1.0, 95% EtOH).

Anal. Calc'd. for $C_{12}H_{18}BrNO_2.HCl$: C, 44.39; H, 5.90; N, 4.32. Found: C, 44.04; H, 5.63; N, 4.40.

EXAMPLE 6

2-Amino-1-(2,5-Dimethoxy-4-methylthiophenyl)butane hydrochloride.

A) 2,5-Dimethoxy-4-methylthiobenzaldehyde

A solution of 6.07 g (0.33 mole) of 1,4-dimethoxy-3-methylthiobenzene in 40 ml of dry $CH_2Cl_2$ under $N_2$ was cooled in an ice bath. To the solution was added 13.02 g (0.05 mole) of $SnCl_4$ over 2 mins. Dichloromethyl methyl ether, 3.45 g (0.03 mole), was then added, dropwise, over 5 mins., and stirring was continued with ice bath cooling for 15 mins. The reaction was allowed to warm to room temperature over 30 mins. and was stirred for an additional 1 hr., at which time HCl evolution has ceased. The mixture was slowly poured onto 15 g of ice in a separatory funnel and the aqueous layer was separated and discarded. The organic phase was washed with 3 × 25 ml of 3N HCl, 3 × 25 ml of saturated NaCl solution, dried ($Na_2SO_4$) and the solvent removed in vacuo. The solid residue was dissolved in $CH_3OH$, and the solvent removed in vacuo. The solid residue was dissolved in $CH_3OH$, filtered, and recrystallized from $CH_3OH-H_2O$ to give 5.86 g (92% ) of yellow needles. TLC (thin layer chromatography) (silica gel-$CHCl_3$) showed only one product. An analytical sample, further purified via the $NaHSO_3$ adduct and recrystallized from $CH_3OH-H_2O$, had a mp of 99°–100° C. Nmr (Nuclear magnetic resonance) ($CDCl_3$) δ2.48 (s, 3H, $SCH_3$), 3.92, 3.97, (2s, 6H, $OCH_3$), 6.74, 7.29 (2s, 2H, ArH), 10.45 ppm (s, 1H, CHO).

The ylidinemalononitrile derivative of the title compound in step A was prepared from equal weights of the benzaldehyde and malononitrile in ethanol with triethylamine catalysis. After recrystallization from ethanol, it had a mp 185°–186° C.

Anal. Calc'd. for $C_{13}H_{12}N_2O_2S$: C, 59.98; H, 4.62; N, 10.76; S, 12.32. Found: C, 59.78; H, 4.83; N, 10.80, S, 11.96.

B) 1-[2,5-Dimethoxy-4-methylthiophenyl]-2-nitro-1-butene.

in the examples or schemes with the proper reagents for those equivalent reagents used therein.

TABLE IV

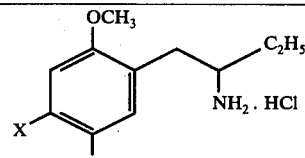

| Compd. No. | X | mp. °C. | % Yield | Opt. Isomer | $[\alpha]365$ (t)[b] | Calcd. C | H | N | Anal. Found C | H | N |
|---|---|---|---|---|---|---|---|---|---|---|---|
| 1 | H | 175 – 177 | 56 | (±) | — | 58.65 | 8.20 | 5.70 | 58.43 | 8.44 | 5.80 |
| 2 | H | 140 – 142 | 83 | R | −44.2° (23) | 58.65 | 8.20 | 5.70 | 58.72 | 8.42 | 5.80 |
| 3 | H | 141 – 144 | 42 | S | +44.3° (24) | 58.65 | 8.20 | 5.70 | 58.75 | 8.38 | 5.61 |
| 4 | Cl | 215 – 216.5 | 53 | R | −60.8° (24) | 51.44 | 6.83 | 5.00 | 51.57 | 6.95 | 5.12 |
| 5 | Br | 206 – 209 | 69 | (±) | — | 44.39 | 5.90 | 4.32 | 44.25 | 5.99 | 4.28 |
| 6 | Br | 240 – 242 | 71 | R | −57.0° (24) | 44.39 | 5.90 | 4.32 | 44.04 | 5.63 | 4.40 |
| 7 | Br | 241 – 243 | 53 | S | +57.6° (24) | 44.39 | 5.90 | 4.32 | 44.51 | 5.88 | 4.62 |
| 8 | CH$_2$OH | 87 – 90 | 74 | (±) | — | 65.24 | 8.84 | 5.85 | 65.52 | 8.68 | 5.61 |
| 9 | CH$_2$OH | 85 – 86 | 82 | R | — | 65.24 | 8.85 | 5.85 | 65.21 | 8.68 | 5.55 |
| 10 | CH(OH)CH$_3$ | 107.5 – 111.5 | 88 | (±) | — | 66.37 | 9.15 | 5.53 | 66.40 | 9.05 | 5.36 |
| 11 | S—CH$_3$ | 220 – 221 | 65 | (±) | — | 53.50 | 7.60 | 4.80 | 53.49 | 7.61 | 4.64 |
| 12 | S—CH$_3$ | 254 – 256 | 10.7 | R | −79.5° (24) | 53.50 | 7.60 | 4.80 | 53.24 | 7.40 | 4.80 |
| 13 | S—CH$_3$ | 254 – 256 | 29.4 | S | +79.9 | 53.50 | 7.60 | 4.80 | 53.31 | 7.37 | 4.73 |

[b]C = 1.0, 95% EtOH 2,5-Dimethoxy-4-methylthiobenzaldehyde (2.3 g), 8.0 ml of 3-nitropropane and 0.45 g of ammonium acetate are mixed in a flask fitted with a condenser and placed on a steam bath for about 5 hours. The excess 3-nitropropane is removed in vacuo to produce orange crystals. The crystals were washed with methanol and filtered to produce the crude product. The crude product is dissolved in 140 ml of boiling ethanol and cooled to produce brilliant orange crystals identified as the title product, 1-[2,5-dimethoxy-4-methylthiophenyl]-2-nitro-1-butene.

C) R-2-Amino-1-(2,5-Dimethoxy-4-methylthiophenyl)butane Hydrochloride.

To a refluxing mixture of 1.4 g of lithium aluminum hydride in 10 ml of anhydrous ether and 40 ml of dry THF is slowly added 1.8 g of 1-[2,5-dimethoxy-4-methylthiophenyl]-2-nitro-1-butene. An additional 20 ml of THF is added to dissolve and wash all the nitro compound into the THF mixture. Refluxing is continued for seven hours. The mixture is cooled and ice water (3.4 ml) slowly added to decompose the excess lithium aluminum hydride. When the decomposition is complete, the mixture is filtered and the solid cake washed with THF. The filtrate is evaporated in vacuo to produce crude 2-amino-1-(2,5-dimethoxy-4-methylthiophenyl)butane. The crude is purified as the hydrochloride salt by recrystallization from isopropanol.

Table IV below represents the physical data of the compounds prepared in the examples, or by substitution

We claim:
1. The compound of the formula

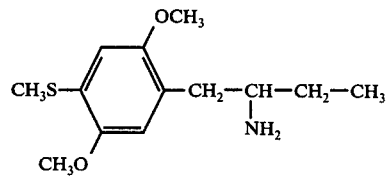

or a pharmaceutically acceptable nontoxic acid addition salt thereof.

2. The compound of the formula

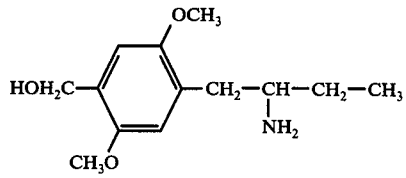

or a pharmaceutically acceptable nontoxic acid addition salt thereof.

3. The hydrochloride salt of the compound of claim 1.

4. The hydrochloride salt of the compound of claim 2.

* * * * *